(12) United States Patent
Nagasawa et al.

(10) Patent No.: US 9,000,163 B2
(45) Date of Patent: Apr. 7, 2015

(54) METHOD FOR PRODUCING AMINOTHIAZOLE DERIVATIVE AND PRODUCTION INTERMEDIATE

(71) Applicant: Zeria Pharmaceutical Co., Ltd., Chuo-ku (JP)

(72) Inventors: Masaaki Nagasawa, Chuo-ku (JP); Kazuyasu Asami, Honjyo (JP); Ryu Nakao, Chuo-ku (JP); Nobuyuki Tanaka, Chuo-ku (JP); Yoshiyuki Aida, Chuo-ku (JP)

(73) Assignee: Zeria Pharmaceutical Co., Ltd., Chuo-ku (JP)

( * ) Notice: Subject to any disclaimer, the term of this patent is extended or adjusted under 35 U.S.C. 154(b) by 0 days.

(21) Appl. No.: 14/065,947

(22) Filed: Oct. 29, 2013

(65) Prior Publication Data

US 2014/0058104 A1    Feb. 27, 2014

Related U.S. Application Data

(62) Division of application No. 11/573,409, filed as application No. PCT/JP2005/015259 on Aug. 23, 2005, now Pat. No. 8,586,761.

(30) Foreign Application Priority Data

Aug. 23, 2004    (JP) .................................. 2004-242759

(51) Int. Cl.
    *C07C 51/377*    (2006.01)
    *C07C 51/347*    (2006.01)
    *C07C 205/60*    (2006.01)
    (Continued)

(52) U.S. Cl.
    CPC ............... *C07C 69/92* (2013.01); *C07C 51/377* (2013.01); *C07D 277/56* (2013.01); *C07C 51/347* (2013.01); *C07C 67/08* (2013.01); *C07C 205/60* (2013.01); *C07D 277/46* (2013.01)

(58) Field of Classification Search
    None
    See application file for complete search history.

(56) References Cited

U.S. PATENT DOCUMENTS 5,981,557 A    11/1999  Nagasawa et al.
7,695,780 B2 *  4/2010  Ohgaru et al. ............... 428/1.31

FOREIGN PATENT DOCUMENTS

DE    1 423 161          1/1976
EP    0 994 108 A1       4/2000
      (Continued)

OTHER PUBLICATIONS

Pinmanee Boontheung, et al., "Base-Promoted Acetal Formation Employing Aryl Salicylates", Arkivoc (Online) Computer File), pp. 95-103, 2001.

Tom Maugh II, et al., "The Role of Intramolecular Bifunctional Catalysis of Ester Hydrolysis in Water", Journal of the American Chemical Society, vol. 93, No. 13, pp. 3237-3248, 1971.

Brian Capon, et al., "The Mechanism of the Hydrolysis of Phenyl Salicylate and Catechol Monobenzoate in the Presence and Absence of Borate Ions", Journal of the Chemical Society, Section B, Physical Organic, vol. 6, pp. 472-478, 1966.

(Continued)

*Primary Examiner* — Sun Jae Yoo
(74) *Attorney, Agent, or Firm* — Oblon, McClelland, Maier & Neustadt, L.L.P.

(57) ABSTRACT

Provided is a method for selectively demethylating a 2-methoxy group. Specifically provided is a production method of a compound represented by formula (7) below through the following reactions.

5 Claims, No Drawings

(51) Int. Cl.
*C07C 67/08* (2006.01)
*C07C 69/92* (2006.01)
*C07D 277/56* (2006.01)
*C07D 277/46* (2006.01)

(56) References Cited

FOREIGN PATENT DOCUMENTS

| JP | 62 501429 | 6/1987 |
|---|---|---|
| JP | 3 204839 | 9/1991 |
| JP | 2000 239224 | 9/2000 |
| WO | 96 36619 | 11/1996 |
| WO | 98 58918 | 12/1998 |

OTHER PUBLICATIONS

F. M. Dean, et al., "Boron Trichloride As a Selective Demethylating Agent", Tetrahedron Letters, No. 35, pp. 4153-4159, 1966.
L. A. Sorbera, et al., "Z-338: Treatment of Non-Ulcer Dyspepsia", Drugs of the Future, XP 002462391, 28(1), 2003, pp. 26-30.
Office Action issued on Nov. 24, 2011 in the corresponding Chinese Patent Application No. 201010571046.0.
Irwin A. Pearl, et al., "Reactions of Vanillin and its Derived Compounds VII Some New Esters of Vanillic Acid and Related Acids", Journal of the American Chemical Society, vol. 71, Issue 3, 1949, pp. 1066-1068.
Extended European Search Report issued Jan. 13, 2011, in Application No. / Patent No. 10010897.6-1211 / 2269975.
Extended European Search Report issued Jan. 14, 2011, in Application No. / Patent No. 10010620.2-1211 / 2275415.
Extended European Search Report issued Jan. 12, 2011, in Application No. / Patent No. 10010896.8-1211 /2269997.
Hiroyasu Nishioka, et al., "Regioselective Dealkylation of 2-Alkoxybenzoic Acid and Its Amide Derivatives with Aliphatic Amines", Synthesis No. 2, XP002612100, 2000, pp. 243-246.
Jerry March, "Advanced Organic Synthesis", Wiley-Interscience, XP002612097, 1992, p. 434.
Database Beilstein [online], Beilstein Institute for Organic Chemistry, CAPON, et al., "2-Hydroxy-5-methoxy-benzoic acid phenyl ester", XP002610770, 1966, Database accession No. 2698910, 2 pages (abstract).
Database Beilstein [online], Beilstein Institute for Organic Chemistry, Pearl, et al., "2-Hydroxy-3-methoxy-benzoic acid phenyl ester", XP002610771, 1949, Database accession No. 3319124, 2 pages (abstract).
Database Beilstein [online], Beilstein Institute for Organic Chemistry, Maugh, et al., "2-Hydroxy-4-methoxy-benzoic acid phenyl ester" XP002610772, 1971, Database accession No. 2741847, 2 pages (abstract).
Database CA [online], Chemical Abstracts Service, John A. Elix, et al., "A novel synthesis of the lichen depsidones divaronic acid and stenosporonic acid and the biosynthetic implications", retrieved from STN, XP002611288, 1987, Database accession No. 1988:131402, 1 page (abstract).
U.S. Appl. No. 14/066,039, filed Oct. 29, 2013, Nagasawa, et al.
U.S. Appl. No. 14/065,862, filed Oct. 29, 2013, Nagasawa, et al.

* cited by examiner

METHOD FOR PRODUCING AMINOTHIAZOLE DERIVATIVE AND PRODUCTION INTERMEDIATE

This application is a divisional of U.S. application Ser. No. 11/573,409 filed Jul. 10, 2013 and which is a National Stage of PCT/JP05/15259.

TECHNICAL FIELD

The present invention relates to a method for selectively demethylating a methoxy group present at the ortho position (2-position) of an aromatic carboxylic acid, and a method for producing an aminothiazole derivative via the demethylation method.

BACKGROUND ART

It is known that compounds in which 2-hydroxybenzoic acids are amide-bonded to 2-aminothiazoles have an excellent gastroprokinetic effect and are useful as prophylactic and therapeutic agents for epigastric indefinite complaints, nausea, vomiting, heartburn, anorexia, abdominal bloating, gastro-oesophageal reflux, and the like (patent documents 1 to 3). Among these compounds, the compound represented by formula (7a) below:

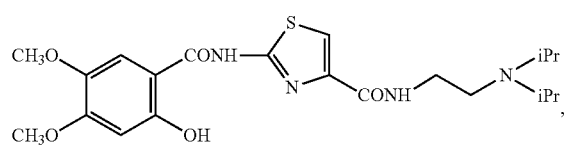

particularly, has a high safety as well as an excellent gastroprokinetic effect and is useful as a prophylactic and therapeutic agent for the above-described various gastroprokinetic disorders.

As a method for producing these 2-hydroxybenzoic acid amide derivatives, patent document 1 adopts a method which involves reacting a 2-methoxybenzoic acid amide derivative with a demethylating reagent such as pyridine hydrochloride to make a 2-hydroxybenzoic acid derivative. However, the demethylation reaction has been problematic to adopt industrially because the reaction produces many side reactions, making it difficult to selectively demethylate only a methoxy group selectively at the 2-position of the amide derivative.

On the other hand, patent documents 2 and 3 describe that the reaction of 2-methoxybenzoic acid amide derivatives with amines such as secondary and tertiary amines selectively demethylates methoxy groups selectively at the 2-position thereof. However, the yield of the demethylation reaction of methoxy groups at the 2-position of the compounds is on the order of 64.6 to 86% and has not yet reached a satisfactory level in view of an industrial method.

[Patent document 1]: WO96/36619
[Patent document 2]: WO98/58918
[Patent document 3]: Japanese Patent Laid-Open No. 2000-239224

DISCLOSURE OF THE INVENTION

Problems to be Solved by the Invention

An object of the present invention is to find a method for selectively demethylating the 2-methoxy group of an aromatic carboxylic acid and provide an industrial method for producing an aminothiazole derivative useful as a medicine via the demethylation method.

Means for Solving the Problems

Accordingly, as a result of various studies of a method for selectively demethylating the 2-methoxy group of an aromatic carboxylic acid having the methoxy group at the 2-position thereof, the present inventor has found that the combination of a particular Lewis acid and a particular solvent enables the selective demethylation of only the 2-methoxy group of the aromatic carboxylic acid even when methoxy groups are present in the 3-, 4-, and 5-positions thereof. The present inventor has further found that when the amidation reaction of a 2-hydroxy aromatic carboxylic acid with a 2-aminothiazole is carried out, the use of the means involving reacting a phenyl ester of the 2-hydroxy aromatic carboxylic acid with the 2-aminothiazole allows the reaction to proceed with an extremely high yield.

The method of the present invention can be illustrated by the following reaction formula.

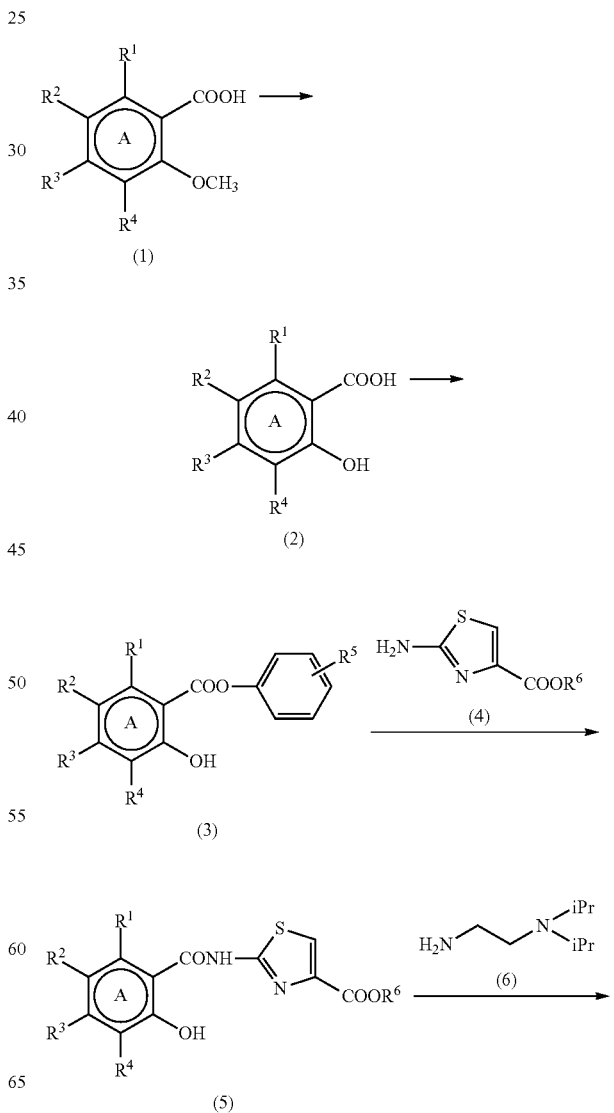

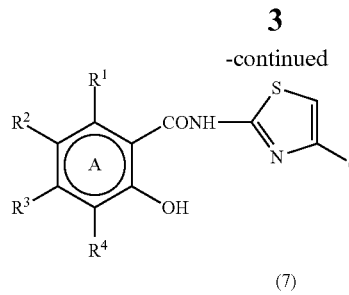

(7)

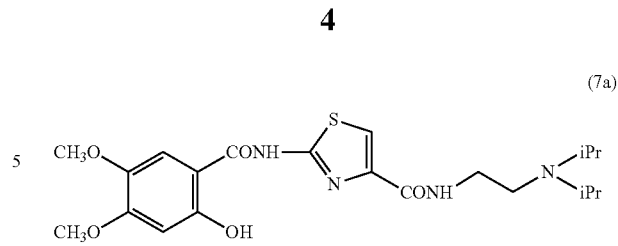

(7a)

(wherein ring A represents a benzene ring or a 6-membered aromatic heterocycle; $R^1$ represents a hydrogen atom, a lower alkyl group, a halogen atom, a nitro group, an amino group, a mono-lower alkylamino group, or a di-lower alkylamino group; at least one of $R^2$, $R^3$, and $R^4$ represents a lower alkoxy group, a lower alkoxylmethoxy group, an aralkoxy group, or an aralkoxylmethoxy group, preferably a methoxy group, and the rest each represents a hydrogen atom, a lower alkyl group, a halogen atom, a nitro group, an amino group, a mono-lower alkylamino group, or a di-lower alkylamino group; $R^5$ represents a hydrogen atom or an electron-withdrawing group; and $R^6$ represents an alkyl group.)

Thus, the present invention provides a production method of a compound of formula (2), comprising reacting a compound of formula (1) with a Lewis acid selected from the group consisting of $BF_3$, $TiCl_4$, and $AlCl_3$ in esteric, ketonic or amidic solvents, with the proviso that an alkali metal bromide or an alkali metal iodide coexists in the case of $BF_3$.

The present invention also provides a production method of a compound of formula (3), comprising reacting a compound of formula (2) with a phenol derivative or a triphenyl phosphite derivative.

In addition, the present invention provides a production method of a compound of formula (5), comprising reacting a compound of formula (3) with a compound of formula (4) under heating at 150° C. or higher or in the presence of a boric acid ester.

Further, the present invention provides a production method of a compound represented by formula (7), comprising reacting a compound represented by formula (5) with N,N-diisopropylethylenediamine in the presence of toluene.

In the above reaction formula showing the method of the present invention, a compound represented by formula (3) is a novel compound, and the compound is extremely important as an intermediate in the method of the invention.

In addition, of the compounds represented by formula (5), a compound wherein $R^6$ is a methyl group, represented by formula (5a):

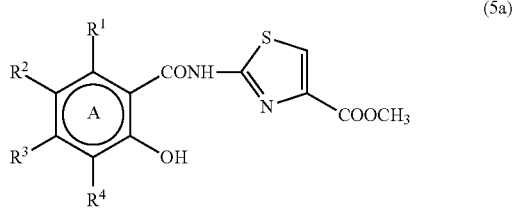

(5a)

(wherein ring A and $R^1$, $R^2$, $R^3$, and $R^4$ are the same as defined above)
is a novel compound, and the compound is also useful as an intermediate in the method of the invention.

It has been also found that the compound represented by formula (7a):

is converted to the hydrochloride thereof, followed by recrystallization from an isopropanol aqueous solution to provide the compound represented by formula (7c):

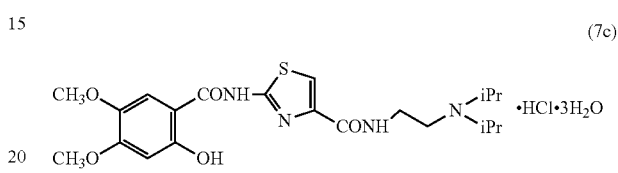

(7c)

stably and efficiently.

Effect of the Invention

According to the present invention, a phenyl ester represented by formula (3) is used as an intermediate to provide a compound represented by formula (7) useful as a gastroprokinetic agent at a high yield and a high purity.

BEST MODE FOR CARRYING OUT THE INVENTION

In the above reaction formula, ring A represents a benzene ring or a 6-membered aromatic heterocycle. The 6-membered aromatic heterocycle is preferably one containing one or two selected from a nitrogen atom, an oxygen atom, and a sulfur atom, and specific examples thereof include a pyridine ring, a pyrimidine ring, a pyrazine ring, a oxazoline ring, and a thiazoline ring; a pyridine ring is preferable. Because these heterocycles have a methoxy group at the ortho position relative to the carboxyl group, for example, as in the formula (1), the ortho position relative to the carboxyl group or carbonyl group comprises a carbon atom. Thus, when the position of the carboxyl group or carbonyl group is defined as the 1-position, specific examples of the heterocycle include a 3-pyridyl group, a 4-pyridyl group, a 5-pyridyl group, a 6-pyridyl group, a 3,5-pyrimidinyl group, and a 4,6-pyrimidinyl group. Among these groups, a 3-pyridyl group, a 4-pyridyl group, a 5-pyridyl group, and a 6-pyridyl group are preferable. Ring A is particularly preferably a benzene ring.

At least one of $R^2$, $R^3$, and $R^4$ is a lower alkoxy group, a lower alkoxylmethoxy group, an aralkoxy group, or an aralkoxylmethoxy group (preferably a methoxy group). According to the present invention, even when one to three of $R^2$, $R^3$, and $R^4$ are each a lower alkoxy group, a lower alkoxylmethoxy group, an aralkoxy group, or an aralkoxylmethoxy group (preferably a methoxy group), only the methoxy group at the 2-position relative to the carboxyl group is selectively demethylated.

Examples of the lower alkoxy groups represented by $R^2$, $R^3$, and $R^4$ include a methoxy group, an ethoxy group, and a methylenedioxy group, and examples of the lower alkoxylmethoxy groups include a methoxylmethoxy group and an ethoxylmethoxy group. Examples of the aralkoxy groups include a benzyloxy group, a methoxybenzyloxy group, and a trityloxy group, and examples of the aralkoxylmethoxy groups include a benzyloxylmethoxy group and a methoxybenzyloxylmethoxy group.

Examples of the lower alkyl groups represented by $R^1$ to $R^4$ include $C_{1-6}$ alkyl groups such as, for example, a methyl group, an ethyl group, an isopropyl group, and an n-butyl group. Examples of the halogen atom include a chlorine atom, a fluorine atom, a bromine atom, and an iodine atom; among these atoms, a chlorine atom, a fluorine atom, and a bromine atom are preferable. Examples of the mono-lower alkylamino group include mono-$C_{1-6}$ alkyl amino groups such as, for example, a methylamino group, an ethylamino group, and an isopropylamino group. Examples of the di-lower alkylamino group include di-$C_{1-6}$ alkylamino groups such as, for example, a dimethylamino group, a diethylamino group, and a diisopropylamino group.

$R^1$ to $R^4$ are preferable when $R^1$ is a hydrogen atom; at least one of $R^2$ to $R^4$ is a lower alkoxy group; and the rest of $R^2$ to $R^4$ are each a lower alkoxy group, a lower alkyl group, a halogen atom, a nitro group, an amino group, a mono-lower alkylamino group, or a di-lower alkylamino group. $R^1$ to $R^4$ are more preferable when $R^1$ and $R^4$ are each a hydrogen atom; $R^2$ and $R^3$ are each a lower alkoxy group, a lower alkyl group, a halogen atom, a nitro group, an amino group, a mono-lower alkylamino group, or a di-lower alkylamino group. $R^1$ to $R^4$ are still more preferable when $R^1$ and $R^4$ are each a hydrogen atom; $R^2$ and $R^3$ are each a lower alkoxy group, and particularly when $R^1$ and $R^4$ are each a hydrogen atom; $R^2$ and $R^3$ are each a methoxy group.

Examples of the electron-withdrawing group represented by $R^5$ include halogen atoms (for example, a fluorine atom), a nitro group, a trifluoromethyl group, a trichloromethyl group, a cyano group, an acetyl group, a sulfonic acid group, and alkylsulfonic acid groups. Among these groups, a nitro group is particularly preferable.

Examples of the alkyl group represented by $R^6$ include $C_{1-8}$ alkyl groups such as, for example, a methyl group, an ethyl group, a propyl group, an isopropyl group, an n-butyl group, a tert-butyl group, and a 2-ethylhexyl group.

Each of the reaction processes is described below.

A compound of formula (1) is reacted with a Lewis acid selected from $BF_3$, $TiCl_4$, and $AlCl_3$ in esteric, ketonic or amidic solvents, with the proviso that an alkali metal bromide or an alkali metal iodide coexists in the case of $BF_3$, to selectively demethylate only the methoxy group at the 2-position to provide a compound of formula (2) at a high yield.

$BF_3$, $TiCl_4$, and $AlCl_3$ may be in the form of a solvate or a hydrate; and $BF_3.Et_2O$, $TiCl_4$, $AlCl_3$, and $AlCl_3.6H_2O$ are preferably used. These Lewis acids are each preferably used in an amount of 1.1- to 4-fold moles, particularly 1.1- to 3-fold moles based on a compound of formula (1) in view of a good balance between reaction selectivity and efficiency. When $BF_3$ is used, NaBr, NaI, KBr, KI, or the like coexists therewith for the proceeding of the selective demethylation reaction of the methoxy group at the 2-position. Lewis acids other than these Lewis acids, such as, for example, Sn, Mg and Zn Lewis acids and Ti $(OiPr)_4$ do not cause the demethylation reaction. The above-described alkali metal salt is preferably used in an amount equimolar to that of the Lewis acid.

The reaction solvent is esteric, ketonic, or amidic solvents. The use of a hydrocarbonic solvent such as toluene does not selectively provide a compound of formula (2) because it also demethylates a methoxy group other than the methoxy group at the 2-position. Examples of the esteric solvent include ethyl acetate, methyl acetate, butyl acetate, and isobutyl acetate; ethyl acetate is preferable. Examples of the ketonic solvent include acetone, 2-butanone, cyclohexanone, and cyclopentanone. Examples of the amidic solvent include dimethylformamide and dimethylacetamide; dimethylformamide is preferable. In this respect, in addition to these solvents, other toluenic solvents may be also used.

The reaction is preferably carried out at 50 to 150° C. for 0.5 to 5 hours, particularly at 60 to 80° C. for 1 to 3 hours.

According to the present invention, only the methoxy group at the 2-position is selectively demethylated to provide a compound of formula (2) at a high yield of 90% or more.

A compound of formula (2) is reacted with a phenol derivative or a triphenyl phosphite derivative to provide a compound of formula (3). When the phenol derivative is used as a phenylation agent, the reaction is preferably performed in the presence of thionyl chloride, phosphorus oxychloride, or the like. When the triphenyl phosphite derivative is used as a phenylation agent, the reaction is preferably conducted in the presence of sulfuric acid, methansulfonic acid, toluenesulfonic acid, trifluoromethanesulfonic acid, or the like. Examples of the phenol derivative include phenol and para-nitrophenol. Examples of the triphenyl phosphite derivative include triphenyl phosphite and tri-para-nitrophenyl phosphite; triphenyl phosphite is preferable.

The phenylation reaction is preferably carried out in a hydrocarbonic solvent such as toluene, xylene, and tetralin at room temperature to 150° C. for 1 to 24 hours, particularly at 90 to 120° C. for 2 to 5 hours.

A compound of formula (3) is reacted with a compound of formula (4) under heating at 150° C. or higher or in the presence of a boric acid ester to provide a compound of formula (5) at an extremely high yield.

When a compound of formula (3) is reacted with a compound of formula (4) under heating at 150° C. or higher, the solvent is preferably tetralin, xylene, dimethylformamide, dimethylacetamide, or dimethylsulfoxide. A reaction temperature of lower than 150° C. prolongs the reaction time. Preferred reaction temperature is 150° C. or higher, particularly 150 to 180° C. The reaction terminates in 2 to 5 hours. This method allows a compound of formula (4) with a high purity to be obtained at a high yield because it does not cause side reactions despite the high reaction temperature.

The boric acid ester is preferably triphenyl borate. The use of triphenyl borate allows a compound of formula (4) with a high purity to be obtained at a high yield because it causes little side reactions. The reaction solvent is preferably toluene or xylene. The reaction is preferably conducted at 80 to 120° C., and terminates in 1 to 5 hours under this condition.

A compound of formula (5) is reacted with N,N-diisopropylethylenediamine (6) in the presence of toluene to provide a compound of formula (7).

This reaction is carried out in toluene to cause little coloration of the reaction solution. As a result, a compound of formula (7) obtained does not become colored, simplifying the after-treatment thereof. The use of xylene or tetralin as a solvent tends to allow the reaction solution to become brownish yellow. This reaction is preferably performed at 50 to 150° C. for 1 to 24 hours, particularly at 90 to 120° C. for 5 to 10 hours.

A production method of the compound of formula (7c) from the compound of formula (7a) is then described. The compound of formula (7a) can be present in the form of various acid addition salts; however, the hydrochloride thereof is preferable. The hydrochloride is present in the form of an anhydride, a monohydrate, and a trihydrate; among these, the trihydrate thereof is excellent particularly in storage stability. The compound of formula (7a) is recrystallized from an isopropanol aqueous solution to provide the trihydrate thereof (7c) stably and efficiently. The isopropanol aqueous solution used preferably has a concentration of 10 to 90%. The compound of formula (7c) obtained using the isopropanol aqueous solution is stable to humidity changes, handling at room temperature, and formulation, and useful as a pharmaceutical raw material.

EXAMPLES

Then, the present invention is described in further detail with reference to Examples. However, the present invention is not intended to be limited thereto.

Example 1

Synthesis of 2-hydroxy-4,5-dimethoxybenzoic acid (2a)

(1) In 10 g of ethyl acetate were suspended 2.0 g of 2,4,5-trimethoxybenzoic acid (1a) and 1.45 g of NaBr in a stream of argon, to which 4.0 g of $BF_3.Et_2O$ was then added dropwise at 25° C., followed by heat stirring at 40° C. for 3 hours. The reaction mixture was cooled with ice, to which 10 mL of water was then added dropwise at 10° C., followed by dropwise adding 7.5 g of a 25% (w/w) sodium hydroxide aqueous solution. Thereto was further added 10 mL of water before stirring, followed by filtering off insoluble inorganic matter. To the separated aqueous layer was dropwise added 3.94 g of 35% hydrochloric acid, followed by stirring for 10 minutes. The precipitated crystal was collected by filtration and washed with water. The resultant crystal was then dried under reduced pressure at 60° C. to provide 1.7 g of 2-hydroxy-4,5-dimethoxybenzoic acid (2a) at a yield of 91%.

$^1$H-NMR(DMSO-$d_6$, δ):3.71 (s,3H), 3.81 (s,3H), 6.56 (s, 1H), 7.17 (s, 1H),11.15-11.30 (bs, 1H), 13.45-13.70 (bs, 1H)

(2) In 30 mL of ethyl acetate was suspended 10 g of the compound (1a) in a stream of argon, to which 6.2 mL of $TiCl_4$ was then added dropwise at 10 to 15° C. under cooling with ice. The reaction mixture was heated to reflux, and stirred for 5 hours. This reaction mixture was cooled, to which 4.9 g of 35% hydrochloric acid was then added dropwise at 24° C. before adding 30 mL of water, followed by heat stirring at 55° C. for one hour. The precipitated crystal was collected by filtration and washed with water to provide 12.45 g of compound (2a) in the form of a wet crystal. The moiety (6.23 g) of the resultant wet crystal was suspended in 15 mL of water, to which 3.52 g of a 25% (w/w) sodium hydroxide aqueous solution was then added dropwise at 18° C., followed by heat stirring at 60° C. for one hour. To the reaction mixture was added 20 mL of ethyl acetate, which was then subjected to liquid-separating operation, followed by dropwise adding 2.19 g of 35% hydrochloric acid to the separated aqueous layer. The precipitated crystal was collected by filtration and washed with water. The resultant crystal was dried under reduced pressure at 60° C. to provide 4.13 g of compound (2a) at a yield of 88%.

(3) In 11 mL of dimethylformamide (DMF) were suspended 2.12 g of compound (1a), 4.82 g of $AlCl_3.6H_2O$, and 2.06 g of NaBr in a stream of argon, which was then heat stirred at 100° C. for 5 hours. The reaction mixture was allowed to stand to cool, to which 10.4 g of 35% hydrochloric acid was then added dropwise before adding 11 mL of water, followed by heat stirring at 70° C. for one hour. The precipitated crystal was collected by filtration and washed with water. The resultant crystal was dried under reduced pressure at 60° C. to provide 1.45 g of compound (2a) at a yield of 73%.

(4) In 20 g of toluene was suspended 6.28 g of $AlCl_3$ in a stream of argon, to which 20 g of DMF was then added dropwise at 26° C. before adding 10.0 g of compound (1a), followed by heat stirring at 85° C. for 1.5 hours. The reaction mixture was cooled, to which 5.89 g of 35% hydrochloric acid was then added dropwise before adding 17.0 g of water, followed by heat stirring at 75° C. for one hour. The precipitated crystal was collected by filtration and washed with water. The resultant crystal was dried under reduced pressure at 60° C. to provide 9.0 g of compound (2a) at a yield of 96%.

Comparative Example 1

(1) To 1 mL of ethyl acetate were added 200 mg of compound (1a) and 387 μL of $BF_3.Et_2O$ in a stream of argon, which was then stirred at 25° C. for 5 hours. However, the reaction did not proceed under these conditions. The reaction also did not proceed at all even under conditions of 50° C. for 5 hours using acetonitrile as a solvent. Thus, it has been found that the use of $BF_3.Et_2O$ requires a reagent such as NaBr.

(2) In 5.0 g of toluene was suspended 500 mg of compound (1a) in a stream of argon, to which 1.27 g of $TiCl_4$ was then added dropwise at 22° C. The reaction mixture was stirred at 70 to 75° C. for one hour.

This reaction also demethylates methoxy groups other than the methoxy group at the 2-position, not enabling the desired compound to be selectively obtained.

(3) In 10 mL of toluene was suspended 500 mg of 2,4,5-trimethoxybenzoic acid in a stream of argon, to which 1.26 g of $AlCl_3$ was then added under stirring at room temperature. The reaction mixture was stirred at 90 to 98° C. for 2 hours.

This reaction also demethylates methoxy groups other than the methoxy group at the 2-position, not enabling the desired compound to be selectively obtained.

From the above (2) and (3), it has been found that the combination of $BF_3.Et_2O$, $TiCl_4$, or $AlCl_3$ and an esteric, ketonic or amidic solvent is important for selective demethylation of the methoxy group at the 2-position.

Example 2

Synthesis of phenyl 2-hydroxy-4,5-dimethoxybenzoate (3a)

(1) In 10 g of xylene were suspended 1.0 g of compound (2a) and 522 mg of phenol, to which 460 μL of $SOCl_2$ was then added dropwise before heating to reflux for 3 hours, followed by further adding 184 μL of $SOCl_2$ and additionally heating to reflux for one hour. The reaction solvent was distilled off, followed by adding methanol to the residue before stirring. The precipitated crystal was collected by filtration to provide 880 mg of phenyl 2-hydroxy-4,5-dimethoxybenzoate (3a) at a yield of 64%.

$^1$H-NMR(DMSO-$d_6$, δ):3.77(s,3H),3.86(s,3H),6.66(s,1H),7.29-7.35 (m,3H),7.40(s,1H),7.46-7.50(m,2H),10.29(s,1H)

(2) In 1.5 g of toluene were mixed 2.35 g of $P(OPh)_3$, 1.5 g of compound (2a), and 40.3 μL of $H_2SO_4$ in a stream of argon, followed by heating the reaction mixture to reflux before stirring for 2.5 hours. The reaction mixture was allowed to stand to cool, to which 5 g of methanol was then added before stirring for 30 minutes, followed by adding 2.5 g of water and stirring for 30 minutes. The precipitated crystal was collected by filtration and dried under reduced pressure to provide 2.0 g of phenyl 2-hydroxy-4,5-dimethoxybenzoate (3a) at a yield of 96%.

Example 3

Synthesis of 2-[(2-hydroxy-4,5-dimethoxybenzoyl)amino]-1,3-thiazole-4-carboxylic acid methyl ester (5a)

(1) In 25 g of toluene were suspended 5.0 g of phenyl 2-hydroxy-4,5-dimethoxybenzoate (3a), 3.75 g of methyl 2-amino-1,3-thiazole-4-carboxylate (4a), and 5.49 g of (PhO)$_3$B in a stream of argon, which was then stirred at 100° C. for 3 hours. Thereto was dropwise added 25 g of methanol at 70° C., followed by heating to reflux for one hour. The reaction mixture was allowed to stand to cool before stirring at 30° C. or lower for one hour, followed by collecting the precipitated crystal by filtration. The crystal was dried under reduced pressure at 60° C. to provide 6.49 g of the monomethanolate of the title compound (5a) at a yield of 96%. The monomethanolate of the title compound (5a) had an extremely high purity of 99.78% as determined by HPLC.

$^1$H-NMR(DMSO-d$_6$, δ):3.19(s,3H),3.79(s,3H),3.83(s,3H),3.84(s,3H),4.05-4.15(bs,1H),6.61(s,1H),7.63(s,1H),8.13(s,1H),11.77 (s,1H),12.40(s,1H)

The drying under reduced pressure was further carried out at 100° C. to provide the title compound (5a).

$^1$H-NMR(DMSO-d$_6$, δ):3.79(s,3H),3.83(s,3H),3.84(s,3H),6.61(s,1H),7.63(s,1H),8.13(s,1H),11.77(s,1H),12.40(s,1H)

(2) In 500 mg of tetralin were suspended 500 mg of phenyl 2-hydroxy-4,5-dimethoxybenzoate (3a) and 433 mg of methyl 2-amino-1,3-thiazole-4-carboxylate (4a) in a stream of argon, which was stirred at 175° C. for 3 hours. After cooling, methanol was added thereto, followed by stirring for one hour. The precipitated crystal was collected by filtration and dried under reduced pressure at 60° C. to provide 620 mg of the monomethanolate of the title compound (5a) at a yield of 92%.

Example 4

Synthesis of 2-[(2-hydroxy-4,5-dimethoxybenzoyl)amino]-1,3-thiazole-4-carboxylic acid methyl ester (5a)

(1) In 2.5 g of xylene were suspended 500 mg of phenyl 2-hydroxy-4,5-dimethoxybenzoate (3a), 288 mg of methyl 2-amino-1,3-thiazole-4-carboxylate (4a), and 204 μL of (MeO)$_3$B in a stream of argon, which was then heated to reflux (at 140° C.) for 3 hours. The reaction mixture was allowed to stand to cool, to which 5 g of methanol was then added dropwise, followed by heating to reflux for one hour. The reaction mixture was cooled with ice and then stirred for one hour, followed by collecting the precipitated crystal by filtration. The crystal was dried under reduced pressure at 80° C. for one hour to provide 505 mg of the monomethanolate of the title compound (5a) at a yield of 80%.

(2) The reaction was carried out as described in (1), using xylene (140° C.) or tetralin (175° C.) as a solvent and employing (PhO)$_3$B in place of (MeO)$_3$B, to provide the monomethanolate of the title compound (5a) at a yield of 85% or 67%, respectively.

The results of (1) and (2) show that the reaction is preferably conducted at 80 to 120° C., in the presence of (PhO)$_3$B.

Comparative Example 3

In 250 mg of xylene were suspended 250 mg of phenyl 2-hydroxy-4,5-dimethoxybenzoate (3a) and 144 mg of methyl 2-amino-1,3-thiazole-4-carboxylate (4a) in a stream of argon, which was then heated to reflux (at 140° C.) for 7 hours. The reaction was not completed. After cooling, methanol was added, followed by stirring for one hour. The precipitated crystal was collected by filtration and dried under reduced pressure at 60° C. to provide 170 mg of the same compound (5a) as that of Example 4 at a yield of 55%.

The results of Comparative Example 3 and Example 3(3) show that the reaction of compound (3a) and compound (4a) by heating is preferably performed at 150° C. or higher.

Example 5

Synthesis of 2-hydroxy-4,5-dimethoxybenzoic acid 4-nitrophenyl ester (3a)

In 5.0 g of toluene were mixed 2.2 g of tris(4-nitrophenyl) phosphite, 1.0 g of 2-hydroxy-4,5-dimethoxybenzoic acid, and 11 μl of H$_2$SO$_4$ in a stream of argon, followed by heating the reaction mixture to reflux before stirring for 2 hours. The reaction mixture was allowed to stand to cool, to which 5 mL of methanol was then added at 40° C. before stirring for 30 minutes, followed by collecting the precipitated crystal by filtration before drying under reduced pressure to provide the title compound (3a) at a yield of 60%.

$^1$H-NMR(CDCl$_3$, δ):3.91(s,3H),3.96(s,3H),6.55(s,1H),7.37(s,1H),7.42(d,2H,J=9.0Hz),8.35(d,2H,J=9.0Hz),10.26(s,1H)

Example 6

Synthesis of 2-[(2-hydroxy-4,5-dimethoxybenzoyl)amino]-1,3-thiazole-4-carboxylic acid methyl ester (5a)

In 1 mL of xylene were suspended 200 mg of 2-hydroxy-4,5-dimethoxybenzoic acid 4-nitrophenyl ester and 119 mg of 2-amino-1,3-thiazole-4-carboxylic acid methyl ester in a stream of argon, which was then stirred at 130° C. for 12 hours. The reaction mixture was allowed to stand to cool, to which 1 mL of methanol was then added, followed by heating to reflux for one hour. The resultant reaction mixture was allowed to stand to cool, followed by collecting the precipitated crystal by filtration at 30° C. or lower before drying under reduced pressure to provide 180 mg of the title compound (5a) at a yield of 80%.

Example 7

Synthesis of N-[2-(diisopropylamino)ethyl]-2-[(2-hydroxy-4,5-dimethoxybenzoyl)amino]-1,3-thiazole-4-carboxamide (compound 7a)

In 30 mL of toluene was suspended 10.81 g of compound (5a) obtained in Example 4, to which diisopropylethylenediamine (6) was then added dropwise at 70° C. in a stream of argon, followed by heat stirring at 100° C. for 5 hours. The reaction mixture was allowed to stand to cool, to which 20 mL of a 10% (w/w) sodium chloride aqueous solution was then added at 75° C. for performing extraction operation. This operation was repeated once again. After removing the aqueous layer, toluene was removed under reduced pressure, followed by diluting the residue with 38 mL of 80% (v/v) aqueous 2-propanol. Thereto was dropwise added 9.22 g of 35% hydrochloric acid to precipitate the hydrochloride of compound (7a). The precipitated crystal was collected by filtration and washed with 2-propanol, and then dried under reduced pressure at 50° C. to provide 14.45 g of the hydrochloride of compound (7a) at a yield of 97%.

$^1$H-NMR(DMSO-$d_6$, δ):1.32 (d, 6H, J=6.4Hz), 1.35 (d, 6H, J=6.4Hz), 3.16 -3.19 (m,2H),3.59-3.67 (m,4H),3.78 (s,3H), 3.82 (s,3H), 6.89 (s, 1H), 7.50 (s, 1H), 7.91 (s, 1H), 8.74 (t,1H,J=5.9Hz),9.70(s, 1H), 11.80 (s, 1H), 12.05-12.15 (bs, 1H)

Comparative Example 5

The reaction was carried out in the same way as that in Example 7 except for the use of xylene or tetralin as a solvent. As a result, the use of xylene or tetralin tended to allow the reaction liquid to be colored brownish yellow although the use of toluene made the liquid colorless or pale yellow.

Example 8

Synthesis of Compound (7)

In 8 mL of aqueous 20% 2-propanol solutin was suspended 2.0 g of compound (7a), which was then heat stirred for complete dissolution. The resultant solution was allowed to stand to cool while continuing the stirring, followed by collecting, by filtration, the crystal precipitated at an internal temperature of 20° C. before washing with aqueous 20% 2-propanol solution. The crystal was dried under reduced pressure at 50° C. to provide 1.8 g of compound (7c) at a yield of 90%.

The resultant crystal (HCl.3H$_2$O) had a value of 9.99 to 10.06%, compared to a theoretical value of 9.98%, in the measurement of the water content using the Karl Fischer method, suggesting that it is a trihydrate. The compound was stable without exhibiting any change in quality due to temperature change and handling at room temperature.

The invention claimed is:

1. A compound represented by formula (3):

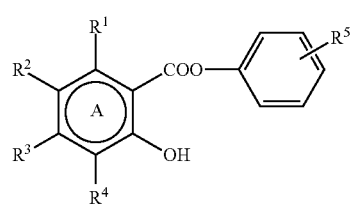

wherein ring A represents a benzene ring or a 6-membered aromatic heterocycle; R1 represents a hydrogen atom; R2 and R3 each represent a methoxy group; R4 represents a hydrogen atom; and R5 represents a hydrogen atom or an electron-withdrawing group selected from a halogen atom, a nitro group, a trifluoromethyl group, a trichloromethyl group, a cyano group, an acetyl group, a sulfonic acid group, and an alkylsulfonic acid group.

2. The compound of claim 1, wherein ring A represents a benzene ring.

3. The compound of claim 1, wherein ring A represents a 6-membered aromatic heterocycle.

4. The compound of claim 1, wherein $R_5$ is a hydrogen atom.

5. The compound of claim 1, wherein $R_5$ is an electron-withdrawing group.

* * * * *